(12) United States Patent
Matsukura et al.

(10) Patent No.: US 11,143,614 B2
(45) Date of Patent: Oct. 12, 2021

(54) GAS SENSOR

(71) Applicant: NGK SPARK PLUG CO., LTD., Aichi (JP)

(72) Inventors: Yusuke Matsukura, Nagoya (JP); Shoji Kitanoya, Kasugai (JP); Masaya Watanabe, Komaki (JP); Daisuke Ichikawa, Minokamo (JP); Masahiro Yamashita, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 259 days.

(21) Appl. No.: 16/050,807

(22) Filed: Jul. 31, 2018

(65) Prior Publication Data
US 2019/0041347 A1 Feb. 7, 2019

(30) Foreign Application Priority Data

Aug. 2, 2017 (JP) .............................. JP2017-149987
Mar. 22, 2018 (JP) .............................. JP2018-054439

(51) Int. Cl.
*G01N 27/18* (2006.01)
*G01N 33/00* (2006.01)
(Continued)

(52) U.S. Cl.
CPC ............. *G01N 27/18* (2013.01); *G01N 25/18* (2013.01); *G01N 27/16* (2013.01);
(Continued)

(58) Field of Classification Search
CPC ...... G01N 27/18; G01N 33/006; G01N 25/18; G01N 27/16; G01N 27/4071;
(Continued)

(56) References Cited

U.S. PATENT DOCUMENTS 6,389,880 B1 * 5/2002 Meyer .................... G01N 27/74
                                                          436/147
8,815,161 B2 * 8/2014 Oishi .................... G01N 33/005
                                                           422/94
(Continued)

FOREIGN PATENT DOCUMENTS

JP      2001-124716 A       5/2001
JP      2001124716 A   *   5/2001

*Primary Examiner* — Marrit Eyassu
(74) *Attorney, Agent, or Firm* — Sughrue Mion, PLLC

(57) ABSTRACT

Disclosed is a gas sensor for detecting a measurement target gas in a measurement gas atmosphere, including first and second sensor elements respectively installed in first and second inner spaces of first and second installation parts. The first and second sensor elements have respective heating resistors connected in series and each has a resistance value that varies with change in temperature thereof so that the concentration of the measurement target gas can be calculated according to a potential between the heating resistors of the first and second sensor elements with the application of a constant voltage. The first and second installation parts are located at such positions that allow a maximum temperature difference of 0.4° C. or less between the first and second inner spaces during change in atmosphere temperature from 0° C. to 80° C.

13 Claims, 13 Drawing Sheets

(51) Int. Cl.
*G01N 25/18* (2006.01)
*G01N 27/16* (2006.01)
*G01N 27/407* (2006.01)

(52) U.S. Cl.
CPC ..... *G01N 27/4071* (2013.01); *G01N 27/4074* (2013.01); *G01N 27/4077* (2013.01); *G01N 27/4078* (2013.01); *G01N 33/006* (2013.01); *G01N 33/0009* (2013.01)

(58) Field of Classification Search
CPC ........... G01N 27/4074; G01N 27/4077; G01N 27/4078; G01N 33/0009; G01N 27/185
USPC ........................................................ 73/25.03
See application file for complete search history.

(56) References Cited

U.S. PATENT DOCUMENTS

| | | | |
|---|---|---|---|
| 2005/0042141 A1* | 2/2005 | Otani | G01N 27/16 422/98 |
| 2005/0265422 A1* | 12/2005 | Bonne | G01N 30/66 374/44 |
| 2008/0185692 A1* | 8/2008 | Salzman | H01L 23/552 257/659 |
| 2011/0168557 A1* | 7/2011 | Park | G01N 27/4074 204/424 |
| 2015/0226688 A1* | 8/2015 | Watanabe | G01N 27/18 73/31.05 |
| 2018/0292338 A1* | 10/2018 | Liu | G01N 27/04 |

* cited by examiner

GAS SENSOR

FIELD OF THE INVENTION

The present invention relates to a gas sensor.

BACKGROUND OF THE INVENTION

There is known a gas sensor capable of detecting and measuring a specific measurement target gas such as combustible gas in a measurement gas atmosphere without being influenced by water (see, for example, Japanese Laid-Open Patent Publication No. 2001-124716). This gas sensor has a pair of first and second sensor elements installed in first and second separate inner spaces. The first inner space in which the first sensor element (as a reference sensor element) is installed is covered by a membrane member, whereas the second inner space in which the second sensor element (as a detection sensor element) is installed is open to the measurement gas atmosphere. The membrane member is of the type having permeability to water vapor but no permeability to the measurement target gas. In such a configuration, both of the first and second sensor elements are placed under the same humidity conditions so as to enable detection and measurement of the measurement target gas without being influenced by humidity.

SUMMARY OF THE INVENTION

When the first and second inner spaces of the gas sensor are located apart from each other, there may arise a large difference between the surrounding temperatures of the first and second sensor elements due to change in environmental temperature. Such a large temperature difference between the first and second sensor elements leads to a large error in the output of the gas sensor.

It is accordingly an object of the present invention to provide a gas sensor with a pair of sensor elements so as to suppress an increase of sensor output error caused by temperature change.

In accordance with a first aspect of the present invention, there is provided a gas sensor for detecting a measurement target gas in a measurement gas atmosphere, comprising:

first and second sensor elements, each of the first and second sensor elements being in the form of a thermal conductivity sensor element having a heating resistor whose resistance value varies with change in temperature thereof, the heating resistors of the first and second sensor elements being connected in series to each other;

a first installation part defining a first inner space in which the first sensor element is installed;

a second installation part defining a second inner space in which the second sensor element is installed;

a casing accommodating therein the first and second installation parts;

a circuit board configured to apply a voltage to the heating resistors of the first and second sensor elements; and a calculation unit configured to calculate a concentration of the measurement target gas in the measurement gas atmosphere according to a potential between the heating resistors of the first and second sensor elements under the application of a constant voltage to the heating resistors by the circuit board, the casing having a casing body formed with an opening to introduce the measurement target gas into an inside of the casing, the first installation part having: a first gas introduction hole formed to provide communication between the first inner space and the inside of the casing; and a membrane member arranged to cover the first gas introduction hole and having permeability to water vapor and substantially no permeability to the measurement target gas, the second installation part having a second gas introduction hole formed to directly introduce the measurement target gas from the inside of the casing into the second inner space, wherein the first and second installation parts are located at such positions that allow a maximum temperature difference of 0.4° C. or less between the first and second inner spaces during change in atmosphere temperature from 0° C. to 80° C. (typically during a change in atmosphere temperature from 0° C. to 80° C. within 30 minutes or even less).

In this aspect, the temperature difference between the first inner space in which the first sensor element is installed and the second inner space in which the second sensor element is installed is maintained at a small level even in the occurrence of environmental temperature change. In other words, the measurement conditions of the first and second sensor elements are close to each other. It is consequently possible to suppress variations in the output of the gas sensor caused due to temperature changes and thereby reduce an error in the output of the gas sensor. Thus, the concentration of the measurement target gas is accurately calculated and outputted by the gas sensor (calculation unit).

In accordance with a second aspect of the present invention, there is provided a gas sensor as described above, wherein the first and second installation parts are constituted by: a ceramic mount base on which the first and second sensor elements are mounted; and a ceramic protective cap covering the ceramic mount base so as to define therebetween the first and second inner spaces.

In this aspect, the difference in thermal expansion coefficient between the ceramic mount base and the ceramic protective cap is made small so that the adhesion of the ceramic mount base and the ceramic protective cap can be prevented from being deteriorated by a thermal shock. It is thus possible to improve the sealing of the inner spaces. It is further possible to simultaneously and easily form the first and the second installation parts so that the first and second inner spaces can be located close to each other for decrease of the temperature difference between these first and second inner spaces.

In accordance with a third aspect of the present invention, there is provided a gas sensor as described above, wherein the casing comprises a filter arranged in the opening and having permeability to the measurement target gas and no permeability to liquid water.

In this aspect, it is possible to suppress the influence of the flow rate of the measurement target gas and improve the output accuracy of the gas sensor.

In accordance with a fourth aspect of the present invention, there is provided a gas sensor as described above, wherein the first installation part comprises a measurement target gas oxidation catalyst that causes oxidation of the measurement target gas flowing into the first inner space.

In the case where the concentration of the measurement target gas is high, there may occur a phenomenon in which the output of the gas sensor slightly decreases with time despite no changes in the concentration of the measurement target gas (see FIG. 12). As a result of extensive researches, the present inventor has found that this sensor output decrease phenomenon takes place with increase in the concentration of the measurement target gas in the first installation part due to slight permeation of the measurement target gas through the membrane member.

In this aspect, however, the measurement target gas oxidation catalyst is arranged to oxide the measurement target gas. The measurement target gas, when passed through the membrane member under such a situation that the concentration of the measurement target gas is high, is oxidized by the measurement target gas oxidation catalyst and thereby removed from the first inner space. It is thus possible to, even in the case where the concentration of the measurement target gas is high, maintain a difference in the concentration of the measurement target gas between the first and second inner spaces and suppress a deterioration in the output of the gas sensor.

In accordance with a fifth aspect of the present invention, there is provided a gas sensor as described above, wherein the measurement target gas oxidation catalyst is arranged inside the first inner space and/or between the membrane member and the first inner space.

In this aspect, it is possible to more reliably remove the measurement target gas flowing into the first inner space.

In accordance with a sixth aspect of the present invention, there is provided a gas sensor as described above, wherein the measurement target gas oxidation catalyst is arranged inside the first gas introduction hole.

In this aspect, the measurement target gas which has passed through the membrane member is efficiently brought into contact with the measurement target gas oxidation catalyst. It is thus possible to reliably suppress a deterioration in the output of the gas sensor.

In accordance with a seventh aspect of the present invention, there is provided a gas sensor as described above, wherein the measurement target gas oxidation catalyst is arranged to cover the first gas introduction hole.

In this aspect, the measurement target gas which has passed through the membrane member is readily and efficiently brought into contact with the measurement target gas oxidation catalyst. It is thus more reliably suppress a deterioration in the output of the gas sensor.

In accordance with an eighth aspect of the present invention, there is provided a gas sensor as described above, wherein the measurement target gas oxidation catalyst is sheet-shaped and arranged on a first inner space-side surface of the membrane member.

In this aspect, it is possible to easily and reliably cover the first gas introduction hole by the measurement target gas oxidation catalyst as the membrane member and the measurement target gas oxidation catalyst are integrally laminated together.

In accordance with a ninth aspect of the present invention, there is provided a gas sensor as described above, wherein the first installation part comprises a sheet-shaped support member that supports at least one of the membrane member and the measurement target gas oxidation catalyst.

In this aspect, it is possible to suppress warpage of the membrane member and the measurement target gas oxidation catalyst and enhance the sealing of the first gas introduction hole. It is also possible to improve the handling of the integrated sheet of the membrane member and the measurement target gas oxidation catalyst.

The other objects and features of the present invention will also become understood from the following description.

DESCRIPTION OF EMBODIMENTS

Hereinafter, embodiments of the present invention will be described below with reference to the drawings.

1-1. First Embodiment

A gas sensor 1 according to the first embodiment of the present invention will be now explained below with reference to FIGS. 1 to 5. The gas sensor 1 is herein configured to detect and measure a specific measurement target gas in a measurement gas atmosphere. The measurement target gas detected and measured by the gas sensor 1 is a combustible gas such as hydrogen, ammonia, carbon monoxide (CO), hydrocarbon (HC) or the like.

Figure 1:
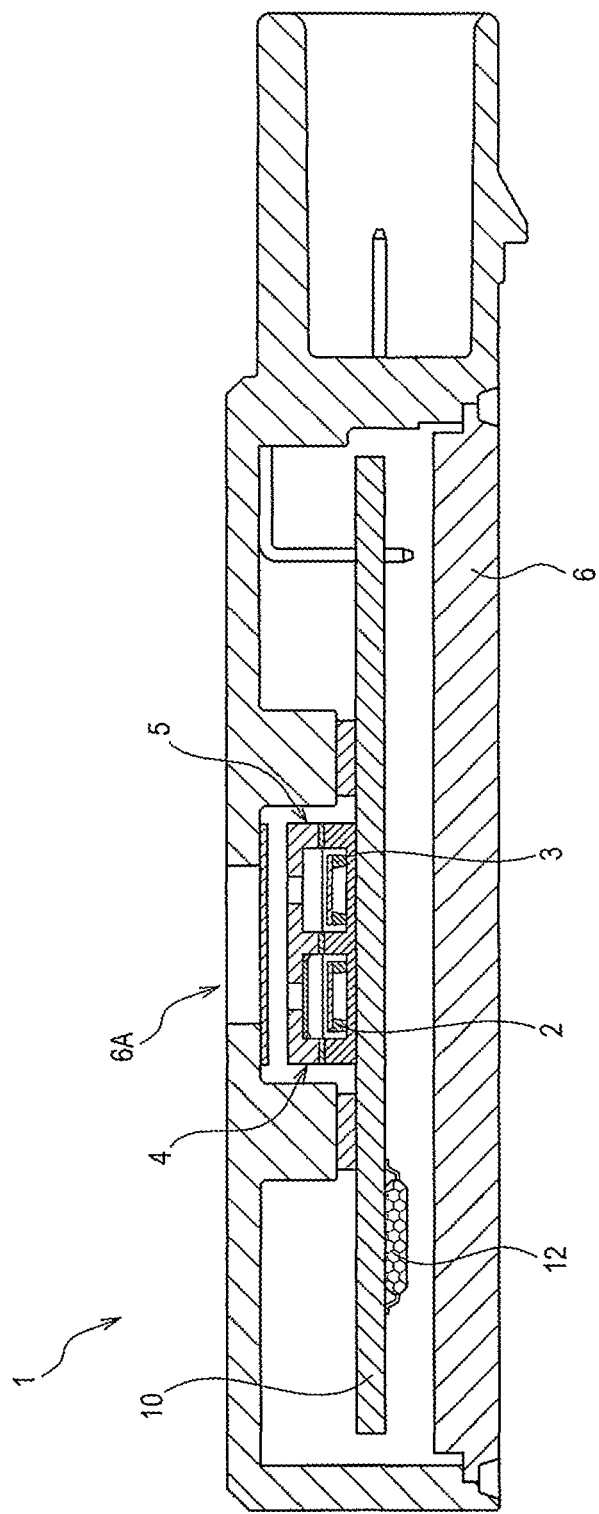
FIG. 1 is a schematic cross-sectional view of a gas sensor according to a first embodiment of the present invention.

As shown in FIG. 1, the gas sensor 1 includes a first sensor element 2, a second sensor element 3, a first installation part 4, a second installation part 5, a casing 6, a circuit board 10 and a calculation unit 12.

First and Second Sensor Elements

Figure 3:
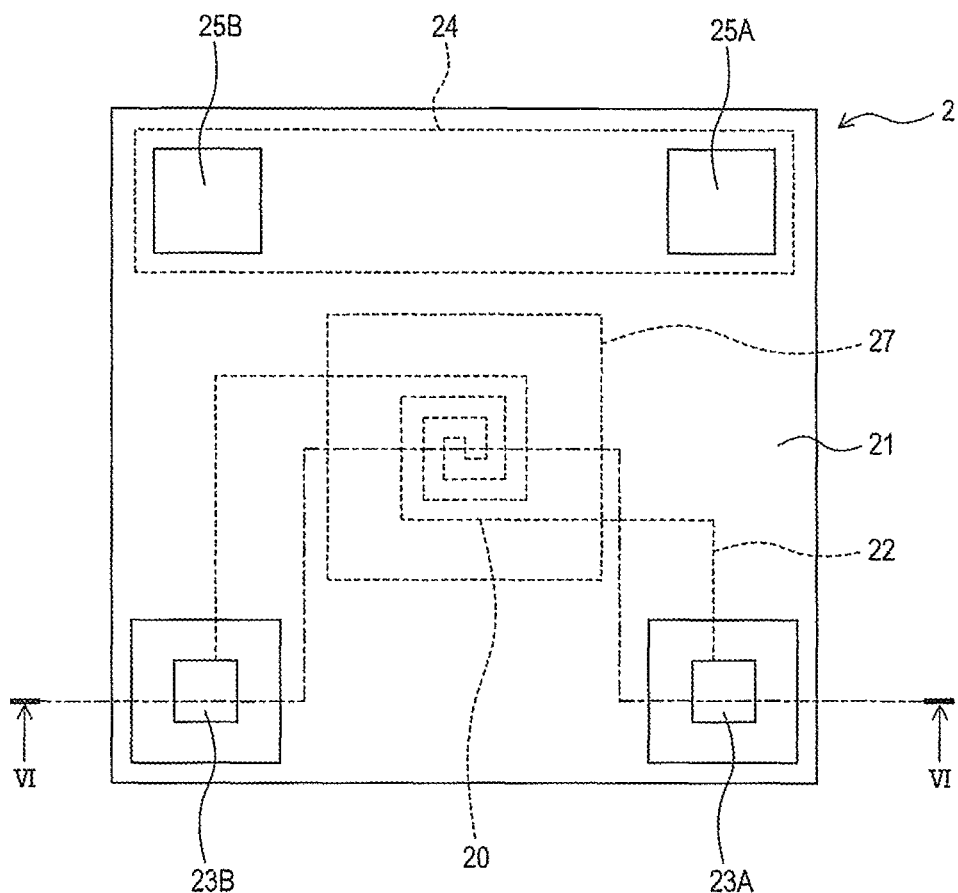
FIG. 3 is a schematic plan view of a sensor element of the gas sensor according to the first embodiment of the present invention.
Figure 4:
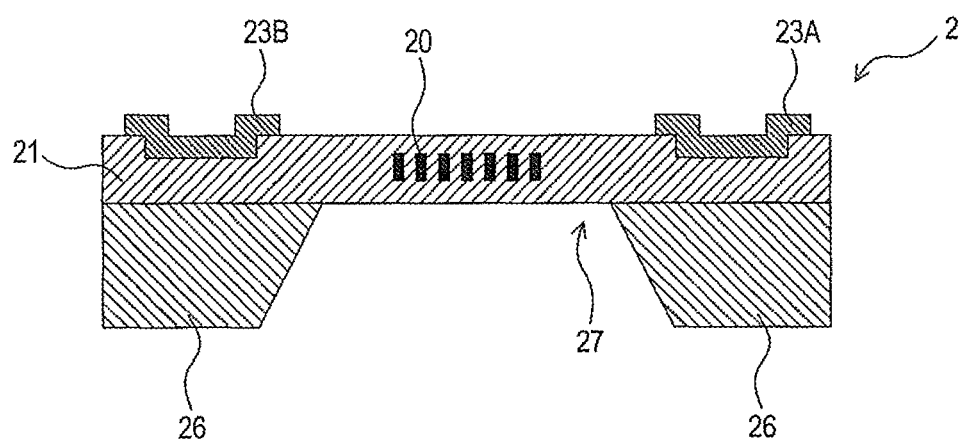
FIG. 4 is a schematic cross-sectional view of the sensor element as taken along line VI-VI of FIG. 3.

In the first embodiment, the first sensor element 2 is in the form of a thermal conductivity type sensor element that does not react with the measurement target gas. As shown in FIGS. 3 and 4, the first sensor element 2 includes a heating resistor 20, an insulating layer 21, a wiring 22, a pair of first electrode pads 23A and 23B, a temperature measuring resistor 24, a pair of second electrode pads 25A and 25B and a substrate 26.

The heating resistor 20 is provided as a spiral pattern conductor and is embedded in a center portion of the rectangular insulating layer 21. The wiring 22 is embedded in the insulating layer 21 and is electrically connected to the heating resistor 20. Further, opposite ends of the wiring 22 are respectively electrically connected to the first electrode pads 23A and 23B. The heating resistor 20 is hence electrically connected to the first electrode pads 23A and 23B via the wiring 22.

The first electrode pads 23A and 23B are disposed on one side of the insulating layer 21. One of the first electrode pads 23A and 23B is connected to a ground, whereas the other of the first electrode pads 23 and 23B is connected to the circuit board 10.

The substrate 26 is made of a silicon material and disposed on the other side of the insulating layer 21. As shown in FIG. 4, a hollow 27 is formed in the substrate 26 at a position corresponding to the heating resistor 20 so as to provide a diaphragm structure with the insulating layer 21 being exposed through the hollow 27.

The temperature measuring resistor 24 is embedded the insulating layer 20 at a position closer to the outer periphery than the heating resistor 20 (more specifically, in one side portion of the insulating layer 21) and is electrically connected to the second electrode pads 25A and 25B.

The second electrode pads 25A and 25B are disposed on the same side of the insulating layer 21 as the first electrode pads 23A and 23B. One of the second electrode pads 25A and 25B is connected to a ground, whereas the other of the first electrode pads 23 and 23B is connected to the circuit board 10.

The heating resistor 20 is made of a conductive material having a high temperature resistance coefficient, and thus has a resistance value that varies with change in temperature thereof. For example, there can be used platinum (Pt) as the material of the heating resistor 20. The temperature measuring resistor 24 is made of a conductive material whose resistance value varies in proportion to temperature. There can be used the same material as the material of the heating resistor 20, such as platinum (Pt), as the material of the temperature measuring resistor 24. The wiring 22, the first electrode pads 23A and 23B and the second electrode pads 25A and 25B can also be made of the same material as the material of the heating resistor 20. The insulating layer 21 can be made of a single insulating material or can be made of different kinds of insulating materials in a multilayer structure. As the insulating material of the insulating layer 21, there can be used silicon oxide ($SiO_2$), silicon nitride ($Si_3N_4$) or the like.

As in the case of the first sensor element 2, the second sensor element 3 includes: a heating resistor 30 whose resistance value varies with change in temperature; and a temperature measuring resistor 24. Since the second sensor element 3 has the same structure as that of the first sensor element 2 in the first embodiment, a detailed explanation of the structure of the second sensor element 3 will be omitted herefrom.

It is preferable that the resistance value of the heating resistor 21 of the first sensor element 2 is equal to that of the second sensor element 3.

First and Second Installation Parts

The first installation part 4 has a first inner space 4A, a first gas introduction hole 4B and a membrane member 4C.

The first inner space 4A is defined in the first installation part 4 such that the first sensor element 2 is installed in the first inner space 4A. The first gas introduction hole 4B is formed in the first installation part 4 so as to provide communication between the first inner space 4A and the inside of the casing 6.

The membrane member 4C is arranged to cover the whole of the first gas introduction hole 4B. Herein, the membrane member 4C shows permeability to water vapor but substantially no permeability to the measurement target gas. The expression "substantially no permeability" means that the amount of permeation of the measurement target gas (on a volume basis) is less than or equal to 1/50 of the amount of permeation of water vapor. As the membrane member 4C, there can suitably be used a fluororesin-based ion exchange membrane. Specific examples of the fluororesin-based ion exchange membrane usable as the membrane member 4C are those available under the trade names of Nafion, Flemion, Aciplex and the like. As the membrane member 4C, there can alternatively be used a hollow fiber membrane capable of separating the measurement target gas and water vapor from each other.

Accordingly, the measurement target gas is not supplied into the first inner space 4A. The first sensor element 2 installed in the first inner space 4A serves as a reference sensor electrode without being exposed to the measurement target gas. The first sensor element 2 is however placed under the same humidity conditions as the second sensor element 3 because water vapor passes through the membrane member 4C.

The first installation part 4 has no opening other than the first gas introduction hole 4B.

On the other hand, the second installation part 5 has a second inner space 5A and a second gas introduction hole 5B.

The second inner space 5A is defined in the second installation part 5 such that the second sensor element 3 is installed in the second inner space 5A. The second gas introduction hole 5B is formed in the second installation part 5 so as to provide communication between the second inner space 5A and the inside of the casing 6.

As the second gas introduction hole 5B is not covered by a membrane member and is open to the measurement gas atmosphere, the measurement target gas is supplied from the inside of the casing 6 into the second inner space 5A through the second gas introduction hole 5B. In other words, the second gas introduction hole 5B enables direct introduction of the measurement target gas into the second inner space 5A.

The second installation part 5 also has no opening other than the second gas introduction hole 5B.

Figure 2:
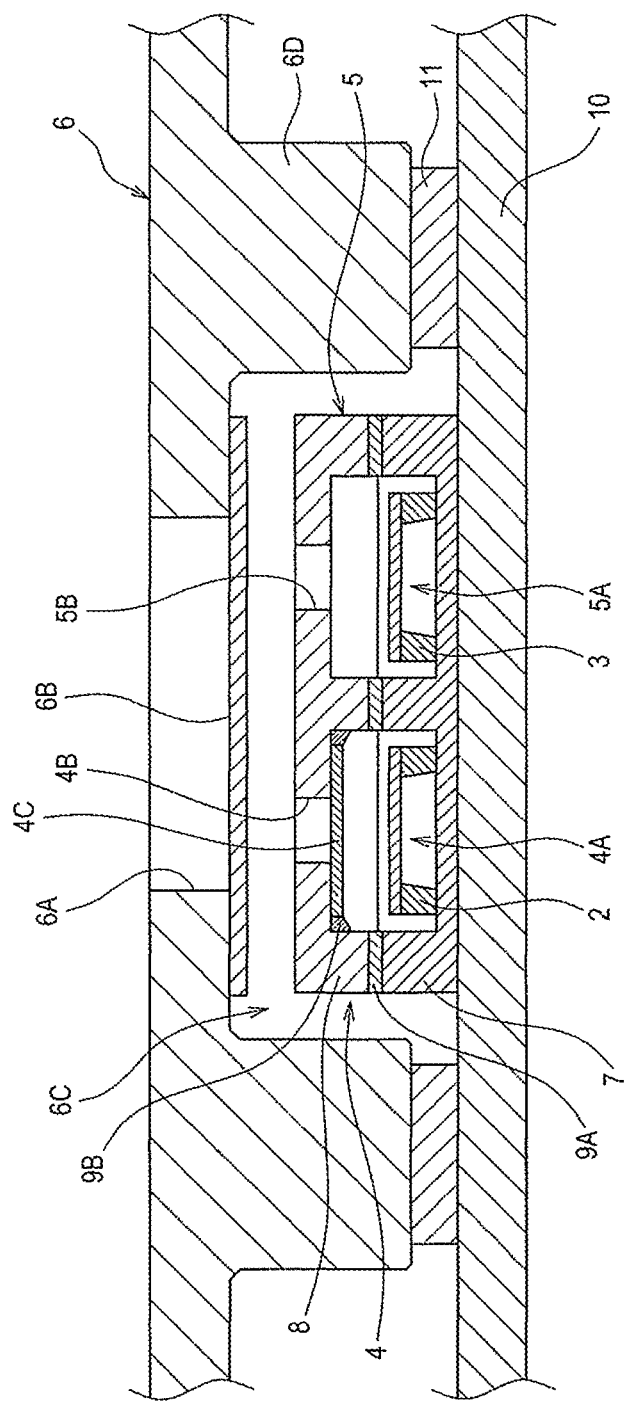
FIG. 2 is an enlarged cross-sectional of a part of the gas sensor in the vicinity of first and second installation parts according to the first embodiment of the present invention.

In the first embodiment, the first and second installation parts 4 and 5 are constituted by a common mount base 7 and a common protective cap (or cover) 8 as shown in FIGS. 1 and 2. Namely, the first and second inner spaces 4A and 5A are separately and adjacently defined, with a partition wall formed therebetween, by mounting the protective cap 8 on the mount base 7. As will be explained later, the first and second installation parts 4 and 5 are situated at such positions as to allow a maximum temperature difference T1 of 0.4° C. or less between the first and second inner spaces 4A and 5A during change in atmosphere temperature from 0° C. to 80° C. typically within 30 minutes or even less.

The mount base 7 is disposed on a surface of the circuit board 10 and is formed with two recess portions in which the first and second sensor elements 2 and 3 are respectively mounted.

The protective cap 8 is formed with two recess portions such that the recess portions of the protective cap 8 are opposed to and face the recess portions of the mount base 7 so as to define therebetween the first and second inner spaces 4A and 5A. The first and second gas introduction holes 4B and 5B are formed through the respective recess portions of the protective cap 8.

Each of the mount base 7 and the protective cap 8 is made of an insulating ceramic material. As the ceramic material of the mount base 7, there can suitably be used alumina. As the ceramic material of the protective cap 8, there can also suitably be used alumina. In the first embodiment, the mount base 7 and the protective cap 8 are made of the same insulating material.

The protective cap 8 is bonded to the mount base 7 so that the mount base 7 and the first and second sensor elements 2 and 3 mounted in the recess portions of the mount base 7 are covered by the ceramic protective cap 8. In the first embodiment, the mount base 7 and the protective cap 8 are bonded together by an adhesive 9A. As the adhesive 9A, there can be used any adhesive containing a thermosetting resin, thermoplastic resin or the like as a main component. For improvement of adhesion between the mount base 7 and the protective cap 8, it is preferable to use an adhesive containing a thermosetting resin as a main component. Specific examples of the thermosetting resin usable in the adhesive are epoxy resin and polyolefin resin. The expression "main component" means a component contained in an amount of 80 mass % or more.

In the first embodiment, the membrane member 4C is bonded by an adhesive 9B to an inner surface of the protective cap 8 facing the first sensor element 2 and thus is fixed over an opening of the first gas introduction hole 4B close to the first inner space 4A. The adhesive 9B for bonding of the membrane member 4C to the protective cap 8 can be the same as the adhesive 9A for bonding of the protective cap 8 to the mount base 7.

Temperature Difference Due to Atmosphere Temperature Change

As mentioned above, the gas sensor 1 is so structured that, when the temperature of the atmosphere in which the gas sensor 1 is placed (that is, the temperature of the measurement gas atmosphere) is changed from 0° C. to 80° C. typically within 30 minutes or even less, the maximum temperature difference T1 between the first and second inner spaces 4A and 5A is 0.4° C. or less in the first embodiment. It is preferable that, when the atmosphere temperature of the gas sensor 1 is changed from 80° C. to 0° C. typically within 30 minutes or even less, the maximum temperature difference T2 between the first and second inner spaces 4A and 5A is 0.4° C. or less. It is more preferable that each of the maximum temperature difference values T1 and T2 is 0.2° C. or less.

It is also preferable that, when the atmosphere temperature of the gas sensor 1 is changed from −40° C. to 100° C. or from 100° C. to −40° C. typically within 30 minutes or even less, the maximum temperature difference T3, T4 between the first and second inner spaces 4A and 5A is 0.4° C. or less.

Each of the maximum temperature difference values T1, T2, T3 and T4 is determined by the following procedure.

The gas sensor 1 is first placed in a thermostat that has been set to a measurement start temperature. Then, the thermostat is heated or cooled until it reaches a measurement end temperature. During the heating or cooling, the temperature difference between the first and second inner spaces 4A and 5A is measured. Based on these measurement results, the maximum value T1, T2, T3, T4 of the temperature difference is determined.

It is feasible to respectively measure the temperatures of the first and second inner spaces 4A and 5A by the temperature measuring resistors 24 of the first and second sensor elements 2 and 3. The temperatures of the first and second inner spaces 4A and 5A may alternatively be measured by any means other than the temperature measuring resistors 24 of the first and second sensor elements 2 and 3, for example, by thermometers placed in the first and second inner spaces 4A and 5A.

The maximum temperature difference values T1, T2, T3 and T4 can be controlled to be equal to or less than the above respective values by adjusting the distance between the first and second installation parts 4 and 5, the materials of the structural members of the first and second installation parts 4 and 5, the thicknesses of the walls defining the first and second inner spaces 4A and 5A, and the like.

Casing

The casing 6 is adapted to accommodate therein the first and second installation parts 4 and 5. The casing 6 has: a casing body formed with an opening 6A for introduction of the measurement target gas into the inside of the casing 6; and a filter 6B arranged in the opening 6A.

More specifically, the casing 6 includes an inner frame portion 6D protruding inward from an inner surface of the casing body so that the circuit board 10 is fixed to the inner frame portion 6D of the casing 6 via a seal member 11 to define therebetween an inner space 6C. The first and second installation parts 4 and 5 (that is, the mount base 7 and the protective cap 8) are accommodated in this inner space 6C.

The opening 6A is formed in the casing body so as to provide communication between the measurement gas atmosphere and the inner space 6C. The measurement target gas introduced from the opening 6A into the inner space 6C is supplied to only the second inner space 5A through the second gas introduction hole 5B. On the other hand, water vapor in the inner space 6C is diffused into both of first and second inner spaces 4A and 5A.

The filter 6B is provided as a water-repellent filter that allows permeation of the measurement target gas but does not allow permeation of water in liquid form. By the arrangement of such a water-repellent filter 6B, the output of the gas sensor 1 can be prevented from being influenced by changes in the flow rate of the measurement target gas. In the first embodiment, the filter 6B is attached to the inner surface of the casing 6 (casing body) so as to cover the opening 6A.

Circuit Board

Figure 5:
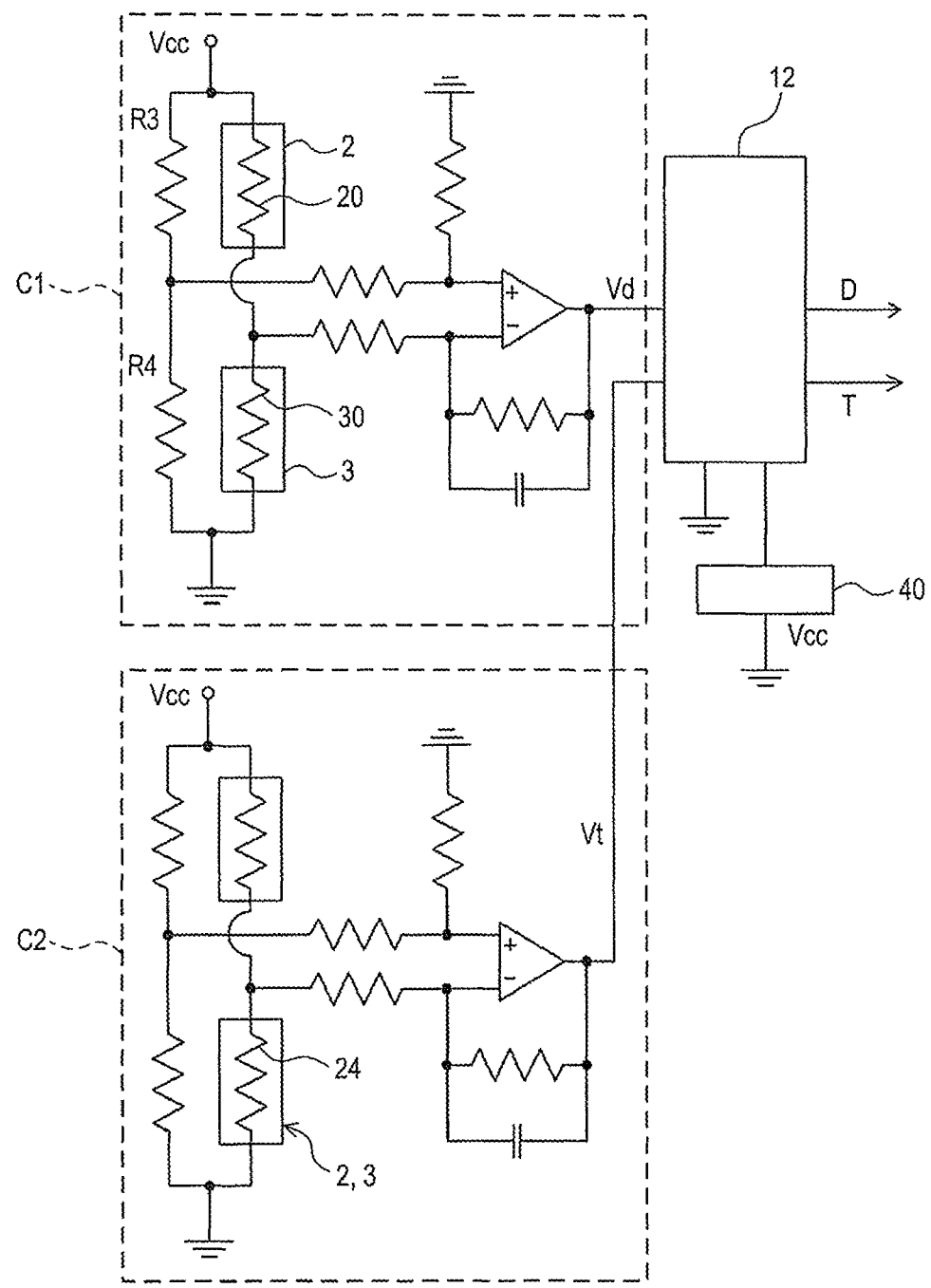
FIG. 5 is a schematic circuit diagram of the gas sensor according to the first embodiment of the present invention.
Figure 6A:
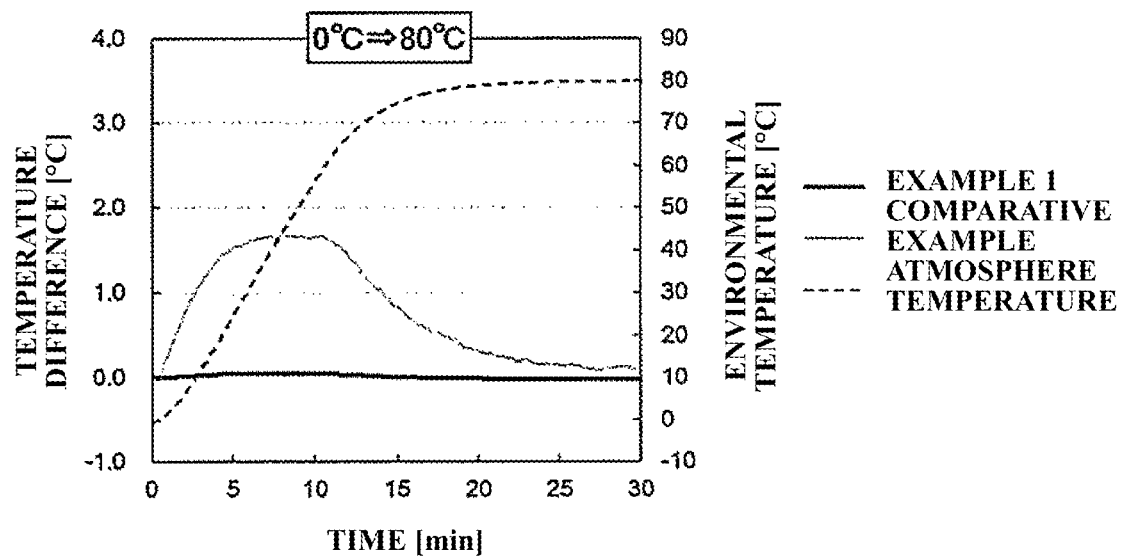
FIG. 6A is a graph showing changes in temperature difference between first and second inner spaces of a gas sensor of Example 1 during change in atmosphere temperature from 0° C. to 80° C.
Figure 6B:
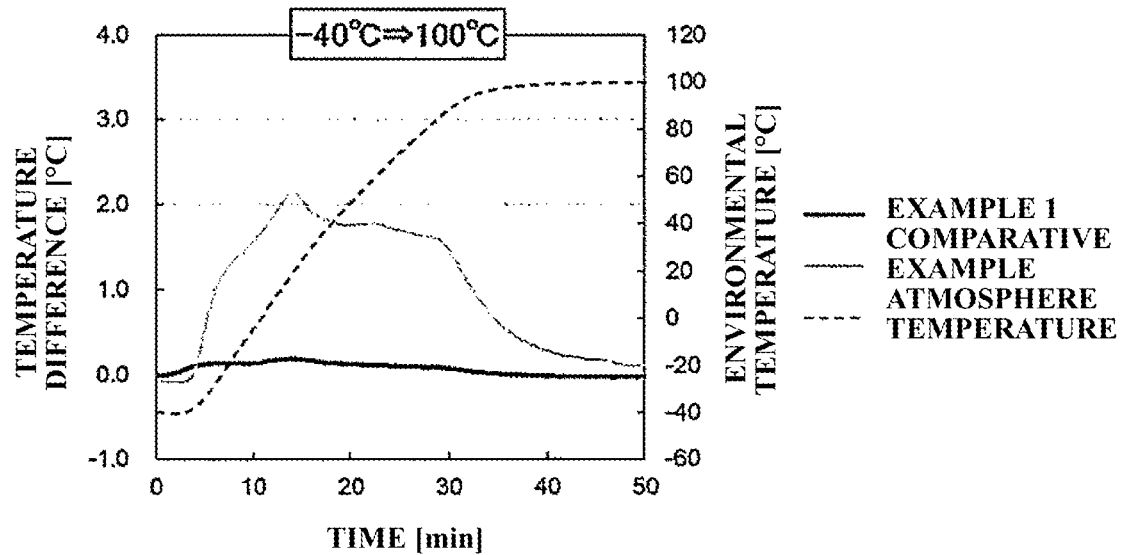
FIG. 6B is a graph showing changes in temperature difference between the first and second inner spaces of the gas sensor of Example 1 during change in atmosphere temperature from −40° C. to 100° C.
Figure 6C:
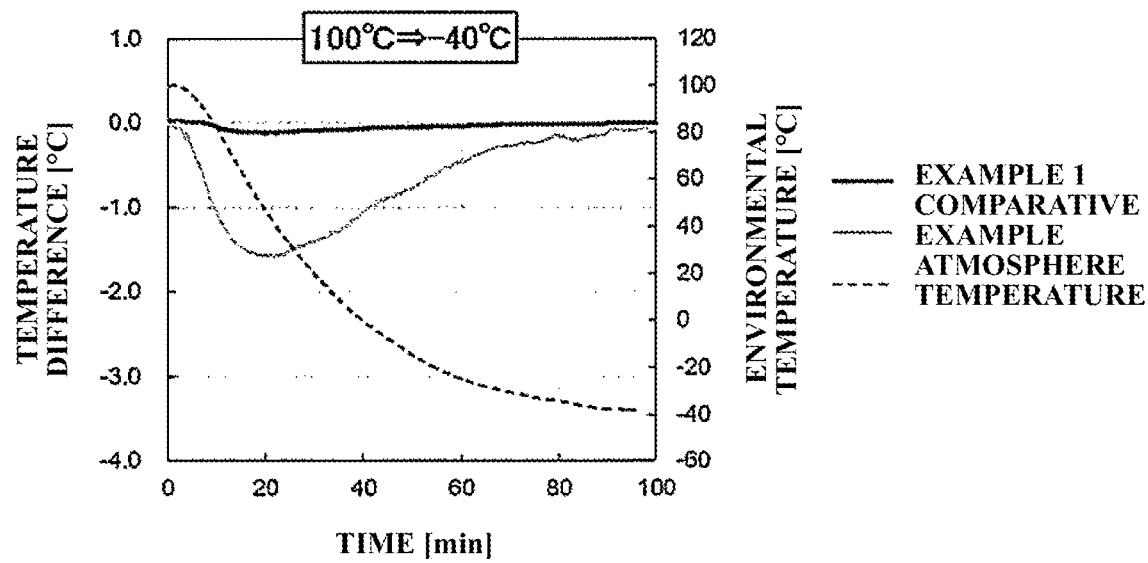
FIG. 6C is a graph showing changes in temperature difference between the first and second inner spaces of the gas sensor of Example 1 during change in atmosphere temperature from 100° C. to −40° C.
Figure 6D:
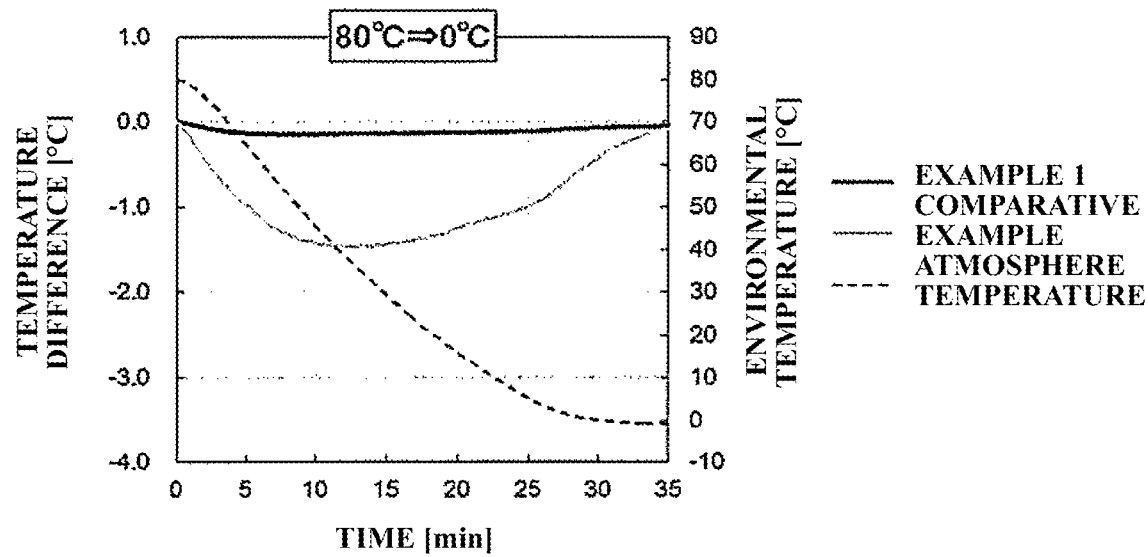
FIG. 6D is a graph showing changes in temperature difference between the first and second inner spaces of the gas sensor of Example 1 during change in atmosphere temperature from 80° C. to 0° C.

The circuit board 10 is plate-shaped and disposed inside the casing 6 so as to form a circuit system with the calculation unit 12 as shown in FIG. 5. The circuit board 10 has: a gas detection circuit C1 that applies a voltage to the heating resistors 20 and 30 of the first and second sensor elements 2 and 3 and generates a gas concentration detection signal Vd according to a potential between the heating resistor 20 of the first sensor element 2 and the heating resistor 30 of the second sensor element 3; and a temperature measurement circuit C2 that applies a voltage to the temperature measuring resistor 24 of the sensor element 2, 3 and generates an temperature detection signal Vt according to a potential difference of the temperature measuring resistor 24 of the sensor element 2, 3.

More specifically, the gas detection circuit C1 has a differential amplifier and fixed resistors R3 and R4. The fixed resistors R3 and R4 are connected in series with each other and respectively arranged in parallel with the heating resistors 20 and 30 of the first and second sensor elements 2 and 3; and the heating resistors 20 and 30 of the first and second sensor elements 2 and 3 are connected in series to each other. With the application of a constant voltage Vcc between the heating resistors 20 and 30, there develop a potential between the heating resistors 20 and 30 and a potential between the fixed resistors R3 and R4. A difference between these potentials is amplified by the differential amplifier and outputted as the gas concentration detection signal Vd from the gas detection circuit C1 to the calculation unit 12.

Further, the temperature measurement circuit C2 has a differential amplifier arranged between the temperature measuring resistors 24 of the first and second sensor elements 2 and 3 and the calculation unit 12. As the resistance value of the temperature measuring resistor 24 varies with change in the temperature of the measurement gas atmosphere, there develops a potential difference across the temperature measuring resistor 24. The potential differences of the temperature measuring resistors 24 of the first and second sensor elements 2 and 3 are respectively amplified by the differential amplifier and outputted as the temperature detection signals Vt from the temperature measurement circuit C2 to the calculation unit 12.

Calculation Unit

The calculation unit 12 is adapted to calculate the concentration D of the measurement target gas in the measurement gas atmosphere based on the gas detection signal Vd and to calculate the temperatures T of the measurement gas atmosphere in the first and second installation parts 4 and 5 (i.e. the temperatures of the first and second inner spaces 4A and 5A) based on the respective temperature detection signals Vt.

The calculation unit 12 and the circuit board 10 are herein supplied with current from a direct-current power supply 40 as shown in FIG. 5.

1-2. Effects

The following effects are obtained in the first embodiment.

(1a) Since T1 is 0.4° C. or less, the temperature difference between the first inner space 4A in which the first sensor element 2 is installed and the second inner space 5A in which the second sensor element 3 is installed is maintained at a small level even in the occurrence of environmental temperature change. In other words, the measurement conditions of the first and second sensor elements 2 and 3 are close to each other. It is consequently possible to suppress variations in the output of the gas sensor 1 caused due to temperature changes and thereby reduce an error in the output of the gas sensor 1.

(1b) By the circuit board 10 and the calculation unit 12, the concentration of the measurement target gas is calculated according to the potential between the heating resistor 20 of the first sensor element 2 and the heating resistor 30 of the second sensor element 3. It is thus possible for the gas sensor 1 to accurately output the concentration of the measurement target gas.

(1c) Further, the mount base 7 and the protective cap 8 are made of ceramic materials so that the difference in thermal expansion coefficient between the mount base 7 and the protective cap 8 is made small. As the adhesion of the mount base 7 and the protective cap 8 can be prevented from being deteriorated by a thermal shock, it is possible to improve the sealing of the first inner space 4A.

(1d) The first gas introduction hole 4B is formed in the ceramic protective cap 8; and the membrane member 4C is attached to the protective cap 8 so as to cover the first gas introduction hole 4B. The membrane member 4C is hence not in contact with a metal material and is prevented from contamination by metal ions. It is thus possible to suppress a deterioration in the water vapor permeability of the membrane member 4C.

(1e) Furthermore, not only the first installation part 4 but also the second installation part 5 are constituted by the mount base 7 and the protective cap 8. It is thus possible to simultaneously and easily form the first and the second installation parts 4 and 5 so that the first and second inner spaces 4A and 5A can be located close to each other for decrease of the temperature difference between these first and second inner spaces 4A and 5A.

(1f) As the filter 6B is arranged in the opening 6A of the casing 6 to prevent the entry of liquid water into the inside of the casing 6, it is possible to suppress the influence of the flow rate of the measurement target gas and improve the output accuracy of the gas sensor 1.

1-3. Second Embodiment

Figure 8:
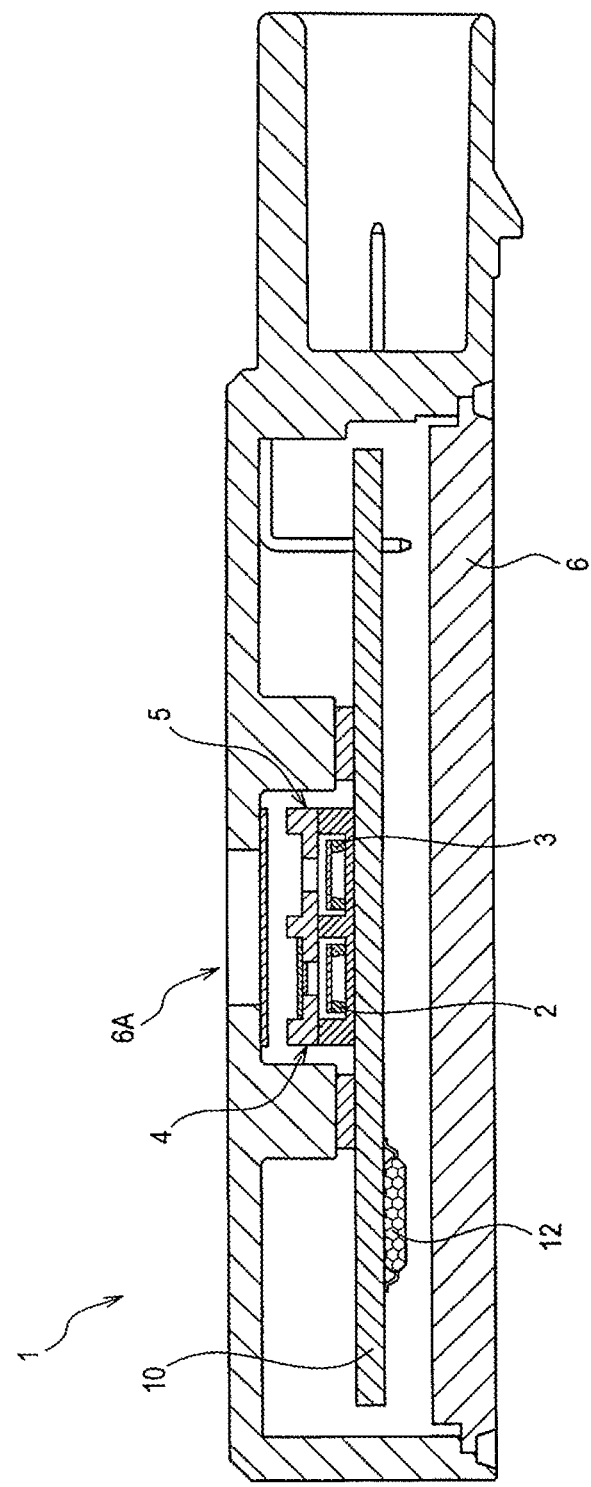
FIG. 8 is a schematic cross-sectional view of a gas sensor according to a second embodiment of the present invention.

The second embodiment of the present invention will be next explained below with reference to FIGS. 8 and 9. As shown in FIG. 8, the gas sensor 1 of the second embodiment is structurally the same as that of the first embodiment. Herein, the same configurations of the second embodiment as those of the first embodiment are designated by the same reference numerals to omit explanations thereof; and the following explanations will focus on differences between the first and second embodiments.

In the second embodiment, the gas sensor 1 is configured to detect and measure hydrogen gas (combustible gas) as the measurement target gas.

Figure 9:
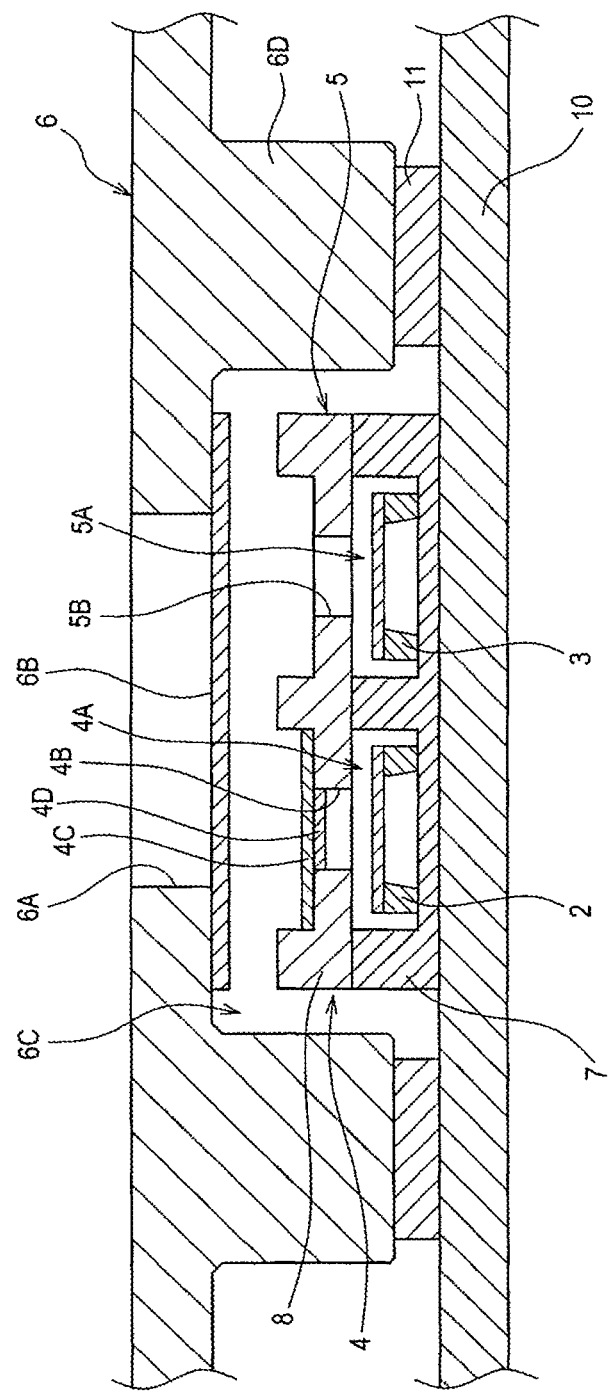
FIG. 9 is an enlarged cross-sectional of a part of the gas sensor in the vicinity of first and second installation parts according to the second embodiment of the present invention.

As shown in FIG. 9, the gas sensor 1 has a hydrogen oxidation catalyst 4D (as a measurement target gas oxidation catalyst) by which hydrogen gas flowing to the first inner space 4A is oxidized to water or water vapor. As such a hydrogen oxidation catalyst 4D, there can be used platinum, palladium, ruthenium, rhodium or alloy thereof. Among others, platinum or platinum-ruthenium alloy can preferably be used.

The hydrogen oxidation catalyst 4D is arranged between the membrane member 4C and the first inner space 4A. More specifically, the hydrogen oxidation catalyst 4D is arranged inside the first gas introduction hole 4B so as to cover the first gas introduction hole 4B. In other words, the hydrogen oxidation catalyst 4D is disposed so as to overlap in position with the first gas introduction hole 4B when viewed in the direction of axis of the first gas introduction hole 4B.

Further, the hydrogen oxidation catalyst 4D has a porous sheet shape supported on a support in the second embodiment. As the support, there can be used activated carbon, fullerene, carbon nanohorn, carbon nanotube or the like. There can alternatively be used a porous ceramic material such as alumina or a metal material such as titanium as the support. The hydrogen oxidation catalyst 5D is arranged on a surface of the membrane member 4C facing the first inner space 4A and then joined to the membrane member 4C by e.g. thermocompression bonding.

As the membrane member 4C and the hydrogen oxidation catalyst 4D are situated to cover the first introduction hole 4B from the outside of the first inner space 4A in the second embodiment, it is feasible to dispose the membrane member 4C and the hydrogen oxidation catalyst 4D after defining the first inner space 4A by reflowing of the base 7 and the protective cap 8. The membrane member 4C and the hydrogen oxidation catalyst 4D are thus prevented from deformation due to expansion of air in the first inner space 4A during the reflowing. Alternatively, the membrane member 4C and the hydrogen oxidation catalyst 4D may be situated to cover the first introduction hole 4B from the side of the first inner space 4A.

The membrane member 4C and the hydrogen oxidation catalyst 4D are placed in a recess portion of the protective cap 8, and are bonded and sealed at peripheries thereof to the protective cap 8 by an insulating adhesive.

In the high hydrogen concentration environment, hydrogen gas which has passed through the membrane member 4C is oxidized to water or water vapor by contact with the hydrogen oxidation catalyst 4D. As the humidity on the inner side (i.e. first inner space 4A-side) of the membrane member 4C becomes high, the water or water vapor is discharged out of the first inner space 4A via the membrane member 4C.

1-4. Effects

In the second embodiment, the following effects are also obtained.

(1g) In the case where the concentration of the hydrogen gas (as the measurement target gas) is high, the hydrogen gas which has passed through the membrane member 4C is oxidized by the hydrogen oxidation catalyst 4D and thereby removed from the first inner space 4A. It is thus possible to, even in the case where the concentration of the hydrogen gas in the measurement gas atmosphere is high, maintain a difference in the concentration of the hydrogen gas between the first inner space 4A (in which the first sensor element 2 is installed as a reference sensor element) and the second inner space 5A (in which the second sensor element 3 is installed as a detection sensor element) and suppress a deterioration in the output of the gas sensor 1.

(1h) As the hydrogen oxidation catalyst 4D is arranged inside the first gas introduction hole 4B so as to cover the first gas introduction hole 4B, hydrogen gas which has passed through the membrane member 4C is efficiently brought into contact with the hydrogen oxidation catalyst 4D. It is thus possible to more reliably suppress a deterioration in the output of the gas sensor 1.

(1i) Further, the hydrogen oxidation catalyst 4D is sheet-shaped and arranged on the first inner space 4A-side surface of the membrane member 4C so that the membrane member 4C and the hydrogen oxidation catalyst 4D can be integrated together. It is thus possible to easily and reliably cover the first gas introduction hole 4B by the hydrogen oxidation catalyst 4D.

2. Modification Examples

Although the present invention has been described with reference to the above embodiments, the above embodiments are intended to facilitate understanding of the present invention and are not intended to limit the present invention thereto. Various changes and modifications can be made to the above embodiments without departing from the scope of the present invention.

(2a) In the gas sensor 1, the mount base 7 and the protective cap 8 are not necessarily made of ceramic materials. The mount base 7 and the protective cap 8 may be fixed together by any means other than the adhesive 9A.

(2b) Although the first and second installation parts 4 and 5 are integrally formed by the common mount base 7 and the common protective cap 8 in the above embodiments, the first and second installation parts 4 and 5 may be formed as separate parts by providing the mount base 7 and protective cap 8 for the first installation part 4 separately from those for the second installation part 5. The first and second installation parts 4 and 5 may be located apart from each other.

Each of the first and second installation parts 4 and 5 is not necessarily formed by the mount base 7 and the protective cap 8 and may be formed by a single hollow structural member.

(2c) The membrane member 4C may alternatively be arranged outside the protective cap 8 so as to cover the first gas introduction hole 4B. Further, the membrane member 4C may be attached to the protective cap 8 by any means other than the adhesive 9A.

(2d) The filter 6B is not necessarily provided in the casing 6. The shape of the casing 6 as shown in FIGS. 1 and 2 is a mere example and can be modified as appropriate.

(2e) In the gas sensor 1, each of the first and second sensor elements 2 and 4 may not be equipped with the temperature measuring resistor 24. Alternatively, the first and second installation parts 4 and 5 may be each provided with any temperature measuring means other than the temperature measuring resistor 24.

(2f) The hydrogen oxidation catalyst 4D may be arranged to cover the first gas introduction hole 4B without being located inside the first gas introduction hole 4B as shown in 10A.

Figure 10A:
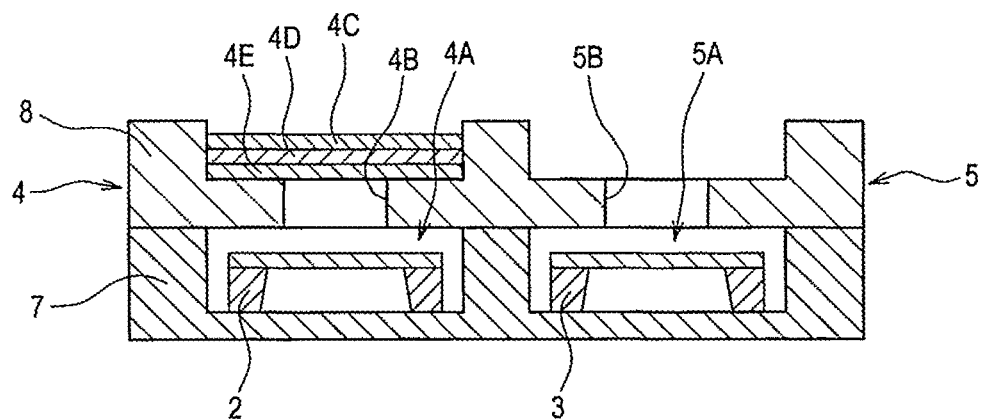
FIG. 10A is an enlarged cross-sectional of a part of a gas sensor in the vicinity of first and second installation parts according to a modification of the second embodiment of the present invention.

(2g) As shown in FIG. 10A, the first installation part 4 may have a sheet-shaped support member 4E that supports the membrane member 4C and the hydrogen oxidation catalyst 4D. In this case, the support member 4E is a porous gas-permeable body made of e.g. carbon material, ceramic material or the like. By such a support member 4E, it is possible to suppress warpage of the membrane member 4C and the hydrogen oxidation catalyst 4D and enhance the sealing of the first gas introduction hole 4B. Further, the membrane member 4C and the hydrogen oxidation catalyst 4D can be integrated together by the support member 4E as one sheet structure for improved handling. Although the support member 4E is laminated on a surface of the hydrogen oxidation catalyst 4D opposite from the membrane member 4C in FIG. 10A, the support member 4E may alternatively be laminated on a surface of the membrane member 4C opposite from the membrane member 4C.

Figure 10B:
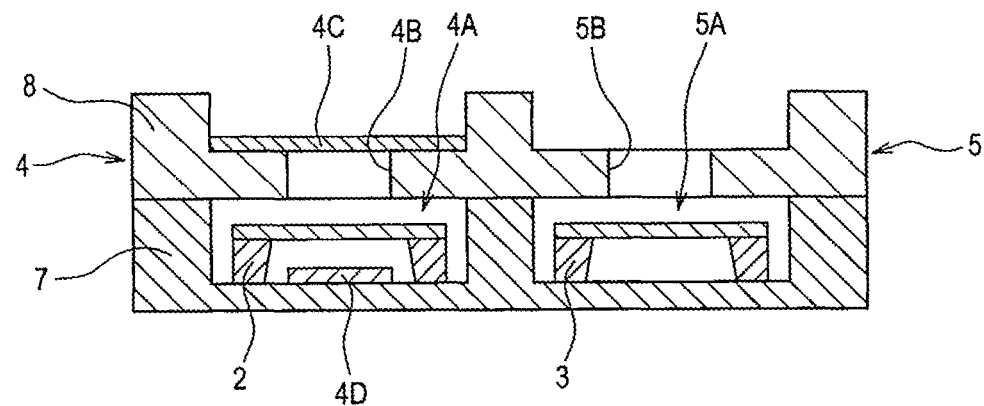
FIG. 10B is an enlarged cross-sectional of a part of a gas sensor in the vicinity of first and second installation parts according to another modification of the second embodiment of the present invention.

(2h) The hydrogen oxidation catalyst 4D is not necessarily arranged to cover the first gas introduction hole 4B. For example, the hydrogen oxidation catalyst 4D may be arranged on an inner wall of the first installation part 4 in which the first gas introduction hole 4B is defined. The hydrogen oxidation catalyst 4D is not also necessarily arranged inside the first gas introduction hole 4B. For example, the hydrogen oxidation catalyst 4D may be arranged inside the first inner space 4A as shown in FIG. 10B. Furthermore, the hydrogen oxidation catalyst 4D is not necessarily sheet-shaped.

(2i) The hydrogen oxidation catalyst 4D is not necessarily arranged between the membrane member 4C and the first inner space 4A or inside the first inner space 4A. For example, the hydrogen oxidation catalyst 4D may be laminated between two membrane members 4C or may be dispersed and included in the membrane member 4C.

(2j) In the above embodiment, it is feasible to divide the function of one component among a plurality of components or combine the functions of a plurality of components into one. Any of the technical features of the above embodiments may be omitted, replaced or combined as appropriate. All of embodiments and modifications derived from the technical scope of the following claims are included in the present invention.

3. Examples

In order to verify the effects of the present invention, Examples 1 to 3 were carried out by the following procedures.

Example 1

In Example 1, a sample of the gas sensor 1 shown in FIG. 1 was produced. The thus-produced gas sensor 1 was placed in a thermostat set at an initial temperature of 0° C. The temperature of the thermostat was then set to 80° C. During a period until the temperature of the thermostat reached 80° C., the temperature difference between the first and second inner spaces 4A and 5A of the gas sensor 1 was measured by means of the temperature heating resistors 24 of the first and second sensor elements 2 and 3. Herein, the voltage Vcc applied was set to 5 V; and the resistance values of the heating resistors 20 and 30 of the first and second sensor elements 2 and 3 were set to 100 ω. Similarly, the temperature difference between the first and second inner spaces 4A and 5A of the gas sensor 1 was measured by changing the temperature of the thermostat from −40° C. to 100° C., from 100° C. to −40° C. and from 80° C. to 0° C. The measurement results are shown in FIGS. 6A to 6D.

Comparative Example

In Comparative Example, a sample of the gas sensor 1 was produced in the same manner as in Example 1, except that the distance between the first and second inner spaces 4A and 5A in Comparative Example was twice that in Example 1. The temperature difference between the first and second inner spaces 4A and 5A was measured under the same measurement conditions as in Example 1. The measurement results are also shown in FIGS. 6A to 6D.

Consideration of Measurement Results

In Example 1, the variation of the temperature difference between the first and second inner spaces 4A and 5A was small under all the measurement conditions as shown in FIGS. 6A to 6D. In particular, the maximum temperature difference between the first and second inner spaces 4A and 5A was 0.4° C. or less under each measurement condition in Example 1. In Comparative Example, by contrast, the variation of the temperature difference between the first and second inner spaces 4A and 5A was large under all the measurement conditions; and the maximum temperature difference between the first and second inner spaces 4A and 5A was 1° C. or more under each measurement condition as shown in FIGS. 6A to 6D.

Figure 7:
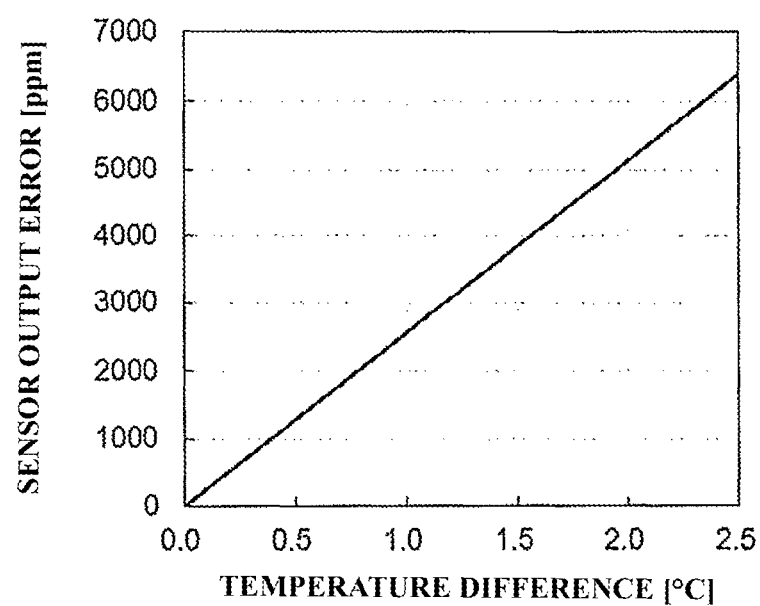
FIG. 7 is a graph showing a relationship of a temperature difference between first and second inner spaces of the gas sensor with an output error of the gas sensor.

As shown in FIG. 7, the temperature difference between the first and second inner spaces 4A and 5A was in proportion to the output error of the gas sensor 1. The larger the temperature difference between the first and second inner spaces 4A and 5A, the larger the output error of the gas sensor 1.

It is understood from FIG. 7 that, in Example 1, the sensor output error remained less than 1000 ppm as the maximum temperature difference between the first and second inner spaces 4A and 5A was 0.4° C. or less under each measurement condition. In Comparative Example, however, the maximum temperature difference between the first and second inner spaces 4A and 5A was more than 2.0° C. under the measurement condition from −40° C. to 100° C. whereby the sensor output error exceeded 5000 ppm.

It has been shown by the above results that it is possible to significantly reduce the output error of the gas sensor 1 and improve the output accuracy of the gas sensor 1 by controlling the temperature difference between the first and second inner spaces 4A and 5A to be 0.4° C. or less.

Examples 2 and 3

Figure 11:
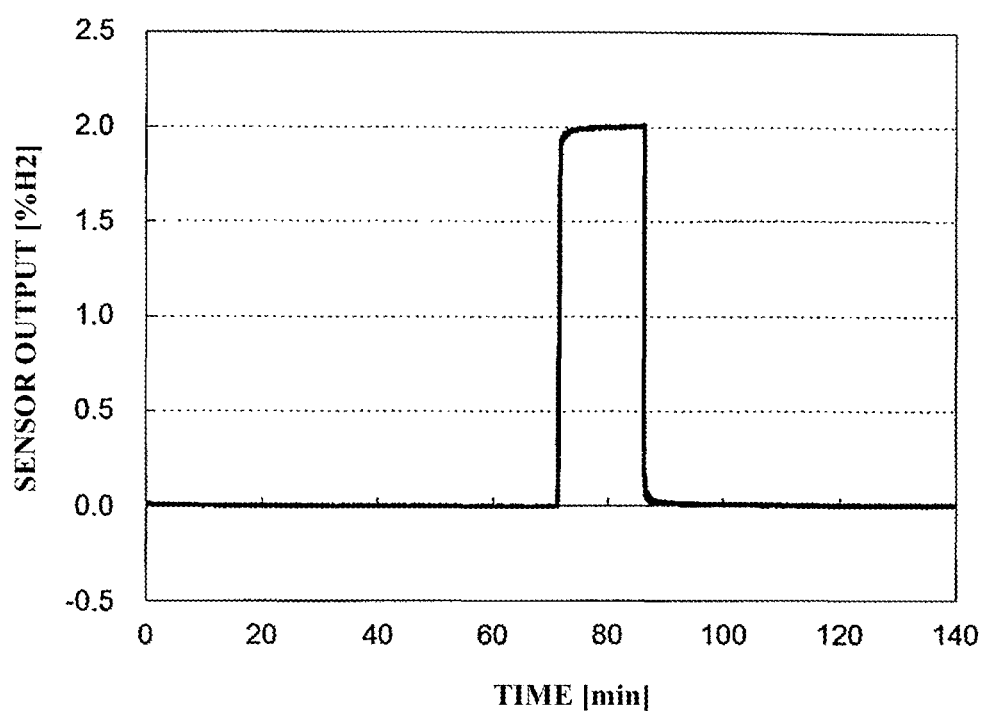
FIGS. 11 and 12 are graphs respectively showing changes in outputs of gas sensors of Examples 3 and 2.

In Example 3, a sample of the gas sensor 1 was produced as shown in FIG. 8. In Example 2, a sample of the gas sensor 1 was produced in the same manner as in Example 3 except for not using the hydrogen oxidation catalyst 4D. In each of Examples 2 and 3, the thus-produced gas sensor 1 was tested by placing the sensor in an environment of relative humidity 95% at 25° C., supplying 2 vol % of hydrogen gas to the sensor for 15 minutes and measuring the output of the sensor. The measurement results are shown in FIGS. 11 and 12.

Consideration of Measurement Results

Figure 12:
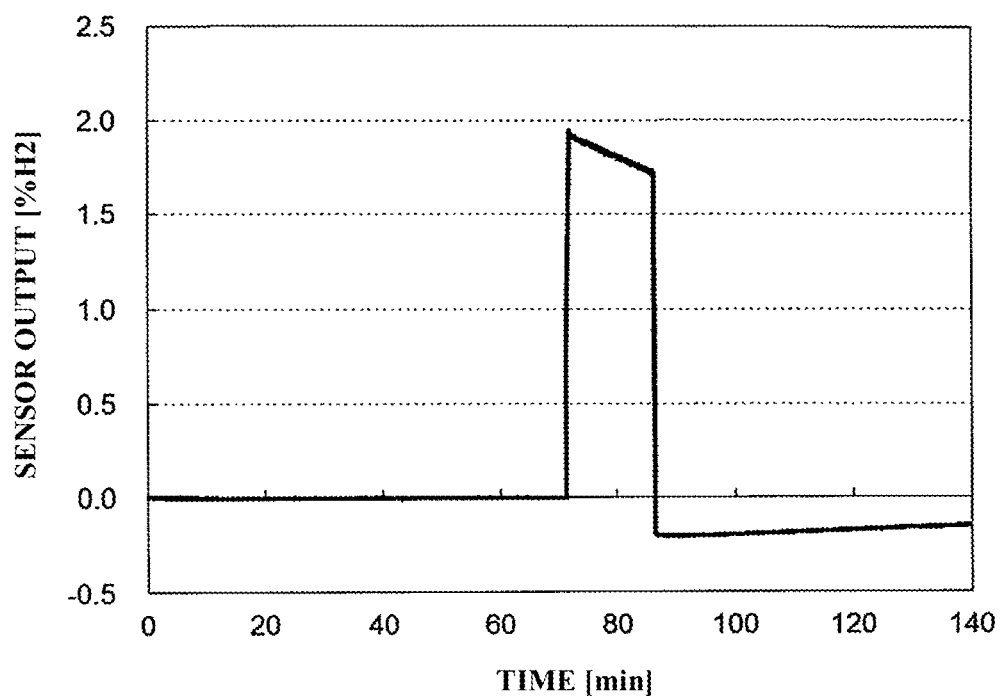

In Example 2, the output of the gas sensor 1 (without the hydrogen oxidation catalyst 4D) was deteriorated with time as shown in FIG. 12. In Example 3, by contrast, the output of the gas sensor 1 (with the hydrogen oxidation catalyst 4A) was maintained constant without deterioration as shown in FIG. 11. The output of the gas sensor 1 was more accurate in Example 3 where the gas sensor 1 was provided with the hydrogen oxidation catalyst 4D than in Example 2 where the gas sensor 1 was not provided with the hydrogen oxidation catalyst 4D.

The entire contents of Japanese Patent Application No. 2017-149987 (filed on Aug. 2, 2017) and No. 2018-054439 (filed on Mar. 22, 2018) are herein incorporated by reference.

What is claimed is:

1. A gas sensor for detecting a measurement target gas in a measurement gas atmosphere, comprising:
   first and second sensor elements, each of the first and second sensor elements being in the form of a thermal conductivity sensor element having a heating resistor whose resistance value varies with change in temperature thereof, the heating resistors of the first and second sensor elements being connected in series to each other;
   a first installation part defining a first inner space in which the first sensor element is installed;
   a second installation part defining a second inner space in which the second sensor element is installed;
   a casing accommodating therein the first and second installation parts;
   a circuit board configured to apply a voltage to the heating resistors of the first and second sensor elements; and a calculation unit configured to calculate a concentration of the measurement target gas in the measurement gas atmosphere according to a potential between the heating resistors of the first and second sensor elements under the application of a constant voltage to the heating resistors by the circuit board, the casing having a casing body formed with an opening such that the opening is open to the measurement gas atmosphere so as to introduce the measurement target gas into an inside of the casing, the first installation part having: a first gas introduction hole formed to provide communication between the first inner space and the inside of the casing; and a membrane member arranged to cover the first gas introduction hole and having permeability to water vapor and substantially no permeability to the measurement target gas, the second installation part having a second gas introduction hole formed to directly introduce the measurement target gas from the inside of the casing into the second inner space, the first and second gas introduction holes being respectively formed in the first and second installation parts at positions opposed to the opening of the casing, wherein the first and second installation parts are located at such positions that allow a maximum temperature difference of 0.4° C. or less between the first and second inner spaces during change in atmosphere temperature from 0° C. to 80° C., and a filter is arranged in the opening of the casing such that the measurement target gas introduced into the inside of the casing passes through the filter, the filter having no permeability to liquid water.

2. The gas sensor according to claim 1, wherein the first and second installation parts are constituted by:

a ceramic mount base on which the first and second sensor elements are mounted; and a ceramic protective cap covering the ceramic mount base so as to define therebetween the first and second inner spaces.

3. The gas sensor according to claim 2,
wherein the circuit board has a plate shape, and the ceramic mount base is mounted on a face of the circuit board.

4. The gas sensor according to claim 2,
wherein a wall of the ceramic mount base separates the first inner space of the first installation part and the second inner space of the second installation part.

5. The gas sensor according to claim 2,
wherein the first and second installation parts are integrally formed by the mount base and the protective cap.

6. The gas sensor according to claim 1,
wherein the first installation part comprises a measurement target gas oxidation catalyst that causes oxidation of the measurement target gas flowing into the first inner space.

7. The gas sensor according to claim 6,
wherein the measurement target gas oxidation catalyst is arranged inside the first inner space and/or between the membrane member and the first inner space.

8. The gas sensor according to claim 7,
wherein the measurement target gas oxidation catalyst is arranged inside the first gas introduction hole.

9. The gas sensor according to claim 7,
wherein the measurement target gas oxidation catalyst is arranged to cover the first gas introduction hole.

10. The gas sensor according to claim 9,
wherein the measurement target gas oxidation catalyst is sheet-shaped and arranged on a first inner space-side surface of the membrane member.

11. The gas sensor according to claim 10,
wherein the first installation part comprises a sheet-shaped support member that supports at least one of the membrane member and the measurement target gas oxidation catalyst.

12. The gas sensor according to claim 1,
wherein the circuit board has a plate shape, and the first installation part and the second installation part are disposed on a face of the circuit board.

13. The gas sensor according to claim 1,
wherein the circuit board is entirely contained within the casing, and a surface of the circuit board is exposed to the measurement target gas introduced inside of the casing.

\* \* \* \* \*